US006689480B2

(12) United States Patent
Shimoyama et al.

(10) Patent No.: US 6,689,480 B2
(45) Date of Patent: Feb. 10, 2004

(54) SURFACE-TREATED PLASTIC ARTICLE AND METHOD OF SURFACE TREATMENT

(75) Inventors: Naoki Shimoyama, Shiga (JP); Mitsuru Yokota, Shiga (JP); Tadahiro Uemura, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/842,402

(22) Filed: Apr. 26, 2001

(65) Prior Publication Data

US 2002/0006521 A1 Jan. 17, 2002

(30) Foreign Application Priority Data

May 10, 2000 (JP) .......................................... 2000-136756

(51) Int. Cl.$^7$ .............................. B32B 27/30; C08J 7/12; G02C 7/04
(52) U.S. Cl. ................ 428/451; 351/160 R; 351/160 H; 359/581; 428/520; 428/522; 523/106; 523/107; 523/108
(58) Field of Search ......................... 351/160 R, 160 H; 359/581; 264/1.1; 427/2.24; 428/451, 500, 520, 522; 523/106, 107, 108

(56) References Cited

U.S. PATENT DOCUMENTS

| 2,936,249 | A | | 5/1960 | Hennemann et al. |
| 5,001,009 | A | | 3/1991 | Whitbourne ................ 428/412 |
| 5,391,589 | A | | 2/1995 | Kiguchi et al. ............. 523/106 |
| 5,662,960 | A | * | 9/1997 | Hostettler et al. ........... 427/2.3 |
| 6,099,852 | A | * | 8/2000 | Jen ............................ 424/429 |
| 6,286,955 | B1 | * | 9/2001 | Akashi ................... 351/160 H |
| 6,428,839 | B1 | | 8/2002 | Kunzler et al. .............. 427/2.1 |

FOREIGN PATENT DOCUMENTS

| EP | 0 461 772 | 12/1991 |
| JP | 1-158412 | 6/1989 |

* cited by examiner

*Primary Examiner*—D. S. Nakarani
(74) *Attorney, Agent, or Firm*—Morrison & Foerster, LLP (57) ABSTRACT

The present invention relates to a surface-treated plastic article including a thin layer composed of a polymer complex on the surface. The surface-treated plastic article can be produced by a treatment with at least one kind of aqueous solutions of polymers having a weight average molecular weight of 200 or more. According to the present invention, the plastic articles, such as contact lenses, having superior transparency, wettability, oxygen permeability, and mechanical properties can be provided.

25 Claims, 1 Drawing Sheet

Fig.1 ATR spectra of plastic article (Ge/75°)

Fig.1 ATR spectra of plastic article (Ge/75°)

US 6,689,480 B2

SURFACE-TREATED PLASTIC ARTICLE AND METHOD OF SURFACE TREATMENT

BACKGROUND OF THE INVENTION

1. Field of the Invention

The present invention relates to a method for surface treatment of a plastic article and a surface-treated plastic article. In particular, the present invention relates to a surface-treated plastic article exhibiting superior hydrophilicity, that is, wettability, and superior deposition resistance, that is, lipid-fouling resistance, etc., which has been surface-treated without degradation of properties as the plastic article. Specifically, the surface-treated plastic article according to the present invention is appropriately used for contact lenses and intraocular lenses, or medical devices, such as catheters and artificial kidneys.

2. Description of the Related Art

In recent years, plastic articles have been proposed for many purposes. Among those, various plastic articles containing silicon or fluorine have been proposed for contact lenses because of the excellent oxygen permeability.

The plastic articles containing silicon or fluorine are, however, insufficient in wettability, and an improvement in the wettability has been demanded. In particular, various methods have been proposed in order to improve the lens performance (fitting characteristics, comfort etc.) in eyes by surface modification of contact lenses. For example, in U.S. Pat. No. 4,214,014, a method, in which the wettability is imparted to a contact lens by a plasma treatment in an oxygen atmosphere, is disclosed. In JP-A-8-227001, a method, in which the wettability is imparted to a silicone containing hydrogel contact lens by a plasma treatment in the atmosphere of oxygen and/or carbon dioxide gas, is disclosed.

The aforementioned conventional techniques improved the wettability, however, there have been problems in that the material quality of the plastic article was degraded due to the oxygen gas. In addition to this, there was a significant problem in that the wettability varied with time due to washings and a long term of use so as to become hydrophobic.

SUMMARY OF THE INVENTION

The present invention includes a method for surface treatment of the plastic article, to get good and stable wettability of the surface without variation over time, thus keeping the good inherent properties of the plastics unchanged. Accordingly, it is an object of the present invention to provide a surface-treated plastic article having high transparency and high oxygen permeability, exhibiting excellent wettability and superior mechanical properties, and appropriately used for, in particular, contact lenses and medical devices such as catheters. It is another object of the present invention to provide a method of surface treatment of the aforementioned plastic article.

The present invention resides in the following features in order to achieve the aforementioned objects. According to a first aspect of the present invention, a method for surface treatment of a plastic article, in which the plastic article is treated with at least one kind of aqueous solutions of polymers having a weight average molecular weight of 200 or more, is provided. According to a second aspect of the present invention, a plastic article, surface-treated with the polymer having a weight average molecular weight of 200 or more, is provided. According to a third aspect of the present invention, a surface-treated plastic article, including a thin layer composed of a polymer complex on the surface, is provided.

DESCRIPTION OF THE PREFERRED EMBODIMENTS

As the surface-treated plastic article according to the present invention, plastic articles primarily composed of homopolymers of various monomers described below, copolymers of these monomers and other monomers, polymers containing silicon in at least one of the main chain and the side chain thereof, for example, polymers containing a siloxane bond or an organic silane group, e.g., trimethylsilyl group, or polymers containing a carbon-fluorine bond can be mentioned.

As specific examples of the monomers for producing the aforementioned polymers, methacrylic acid (hydroxy)alkyl esters, for example, methyl methacrylate and 2-hydroxyethyl methacrylate, methacrylic esters containing silicon, for example, tris(trimethylsiloxy)silylpropyl methacrylate, methacrylic esters containing fluorine, and polydimethylsiloxane having a double-bond at a single terminal or at each of both terminals, can be mentioned.

As the monomer which can copolymerize, mono-functional monomers, for example, methacrylic acid ester-based monomers, aromatic vinyl monomers, and heterocyclic vinyl monomers, multi-functional monomers, for example, di-functional methacrylates, tri-functional methacrylates, tetra-functional methacrylates, aromatic divinyl monomers, and aromatic diaryl monomers, etc., can be mentioned.

As specific examples of the mono-functional monomer, alkyl methacrylates, for example, methyl methacrylate and ethyl methacrylate, carboxylic acids, for example, methacrylic acid, cycloalkyl methacrylates, for example, cyclohexyl methacrylate, halogenated alkyl methacrylates, for example, trifluoroethyl methacrylate and hexafluoroisopropyl methacrylate, hydroxyalkyl methacrylates having a hydroxyl group, for example, 2-hydroxyethyl methacrylate and 2,3-dihydroxypropyl methacrylate, acrylamides, for example, acrylamide, N,N-dimethylacrylamide, and N,N-diethylacrylamide, methacrylic acid esters having a siloxanyl group, for example, tris(trimethylsiloxy)silylpropyl methacrylate and bis(trimethylsiloxy)methylsilylpropyl methacrylate, aromatic vinyl monomers, for example, styrene and vinylpyridine, styrene derivatives having a siloxanyl group, for example, tris(trimethylsiloxy)silylstyrene, styrene derivatives having fluorine, for example, pentafluorostyrene, and heterocyclic vinyl monomers, for example, N-vinyl pyrrolidone, can be mentioned.

As specific examples of the di-functional monomer, ethylene glycol dimethacrylate, diethylene glycol dimethacrylate, bisphenol A dimethacrylate, bisphenol A dimethacrylate ethylene oxide adduct or urethane-modified substances thereof, propylene glycol dimethacrylate, glycerol dimethacrylate, neopentyl glycol dimethacrylate, etc., can be mentioned. As specific examples of the tri-functional monomer, trimethylolpropane trimethacrylate, trimethylolpropane trimethacrylate ethylene oxide adducts, etc., can be mentioned. As specific examples of the tetra-functional monomer, tetramethylolmethane tetramethacrylates, etc., can be mentioned. As specific examples of the aromatic divinyl monomers, divinylbenzene, etc., can be mentioned. As specific examples of the aromatic diaryl monomers, diaryl phthalate, etc., can be mentioned. As specific examples of other multi-functional monomers, bismaleimide, aryl methacrylate, etc., can be mentioned.

The plastic article used in the present invention may be water containing hydrogel, may be a rubber-like polymer (elastomer) not containing water, or may be a hard polymer containing no water or containing small amounts of water depending on the rates of these monomers in copolymerization and the kinds of used monomers.

The surface-treated plastic article according to the present invention may be transparent or may be opaque, although since the hydrogel and the plastic article containing at least one of a silicon atom and a fluorine atom are superior in oxygen permeability, those are preferably used for the optical articles, so that the transparency is preferably imparted thereto.

Regarding the polymer constituting the surface-treated plastic article according to the present invention, in the case in which the polymer is hydrogel, the combination of a hydrophilic monomer and a cross-linking agent and the combination of a hydrophobic monomer, a hydrophilic monomer, and a cross-linking agent are preferably used. For example, the combination of 2-hydroxyethyl methacrylate and ethylene glycol dimethacrylate, and the combination of 2,3-dihydroxypropyl methacrylate, methyl methacrylate, and diethylene glycol dimethacrylate are mentioned. In the case in which the hydrogel contains at least one of a silicon atom and a fluorine atom, the combinations of methacrylic acid esters having siloxanyl group, for example, tris(trimethylsiloxy)silylpropyl methacrylate or a silicone component, for example, polydimethylsiloxane containing double bonds at both ends, a component containing fluorine, for example, hexafluoroisopropyl methacrylate, a hydrophilic component, for example, N,N-dimethylacrylamide and N-vinyl pyrrolidone, and a cross-linking agent are mentioned. In the case of plastic articles which contains substantially no water and contains the component containing silicon and/or fluorine atom, the content of the component containing the silicon atom or the fluorine atom, may be 100% by weight, although the content is preferably 5% by weight or more, more preferably is 30% by weight or more, from the view point of the maintenance of the balance between the oxygen permeability and the mechanical properties.

Regarding the method for the polymerization, conventional methods can be used. The surface-treated plastic article according to the present invention may contain an ultraviolet absorbent, a coloring matter, colorant, etc.

In the production of the plastic article used in the present invention, in order to facilitate the polymerization, thermal polymerization initiators or photopolymerization initiators, typified by peroxides and azo compounds, are preferably blended. In the thermal polymerization, the initiator exhibiting optimal decomposition performance at the desired reaction temperature is selected and used. In general, the peroxide-based initiators and azo-based initiators, having a half-life of 10 hours at a temperature of 40° to 120° C., are appropriate. As the photopolymerization initiator, carbonyl compounds, peroxides, azo compounds, sulfur compounds, halogen compounds, metallic salts, etc., are mentioned. These polymerization initiators are used solely or as mixtures, in an amount up to about 1% by weight.

In the production of the plastic article used in the present invention, polymerization solvents can be used. As the solvent, various organic and inorganic solvents can be applied. Although not specifically limited, for example, water, various alcohol solvents, e.g., methanol, ethanol, propanol, 2-propanol, butanol, and tert-butanol, various aromatic hydrocarbon-based solvents, e.g., benzene, toulene, and xylene, various aliphatic hydrocarbon-based solvents, e.g., hexane, heptane, octane, decane, petroleum ether, kerosene, ligroin, and paraffin, various ketone-based solvents, e.g., acetone, methyl ethyl ketone, and methyl isobutyl ketone, various ester-based solvents, e.g., ethyl acetate, butyl acetate, methyl benzoate, and dioctyl phthalate, and various glycol ether-based solvents, e.g., diethyl ether, tetrahydrofuran, dioxane, ethylene glycol dialkyl ether, diethylene glycol dialkyl ether, triethylene glycol dialkyl ether, tetraethylene glycol dialkyl ether, and polyethylene glycol dialkyl ether, can be mentioned. These can be used solely or as mixtures.

The plastic article used in the present invention can be produced by, for example, the following method.

That is, polymers may be molded into rods and plates at first, and then, may be worked into desired shape. Other known techniques, such as the mold polymerization and the spin cast polymerization, may be used. Regarding the molding into fibers and films, polymers may be molten or dissolved in solvents, and then, may be spun or subjected to the extrusion molding. As an example, the case in which the plastic article used in the present invention is produced by the mold polymerization will be explained below. The monomer mixture of the aforementioned monomer composition and the polymerization initiator are put in the space between a pair of molds having specified shapes, and are molded into the shape of the molds by the photopolymerization or the thermal polymerization. The molds are made of resins, glass, ceramics, metals, etc. In the photopolymerization, optically transparent materials are used, and usually, the resins and the glass are used. In the production of the plastic articles, in many cases, a pair of faced molds form the space, and a monomer mixture is put into the space, although a gasket may be concurrently used for imparting specified thickness to the plastic article and for preventing monomer mixture liquid put into the space from leaking. The molds, in which the monomer mixtures are put into the spaces, may be subsequently subjected to irradiation of an activation ray, such as an ultraviolet ray, or may be subjected to heating and polymerization in an oven or a liquid bath. A Double-polymerization method in which the thermal polymerization is performed after the photopolymerization, or, on the contrary, the photopolymerization is performed after the thermal polymerization, may be concurrently used. Regarding the photopolymerization, in general, the light, primarily including the ultraviolet ray, using, for example, a mercury lamp and an insect collection lamp as the light source, is irradiated for a short time, usually within one hour. Regarding the thermal polymerization, in order to maintain the optical uniformity and quality of the plastic article, and to improve the reproducibility, it is appropriate to gradually raise the temperature from the vicinity of room temperature to 60° to 200° C. over a period of time several hours to several tens of hours.

It was discovered that very simple treatment of immersing the plastic articles in at least one kind of aqueous solutions selected from the group consisting of high molecular weight acids, high molecular weight bases, and water-soluble polymers, each having the weight average molecular weight of 200 or more, exhibited surprising effects of improving the hydrophilicities (water wettabilities) of the plastic articles, and of maintaining these, so that the present invention was made.

In particular, the high molecular weight acids and bases having average molecular weights of 500 or more are preferably used from the viewpoint of preventing the plastic articles from degrading due to the acids and the bases. Furthermore, regarding the treatment of the hydrogel plastic articles, the high molecular weight acids and bases having average molecular weights of 1,000 or more are preferably used.

Regarding the treatment with aqueous solutions of the polymer having the weight average molecular weight of 500 or more, since the polymers do not penetrate into the inside of the plastic articles, the plastic articles are not likely to degrade due to the cleavage of at least one of the main chains and side chains.

In order to effectively improve the hydrophilicity (wettability) and to maintain the effects for a long term, the polymer aqueous solution having a pH of 4 or less or a pH of 8 or more is preferably used. The treatment with the polymer aqueous solution, having a pH of more than 4 and less than 8, may take a long time to produce the hydrophilicity, and in some cases, sufficient hydrophilicity may not be produced.

The treatment temperature is usually 1° to 99° C., and preferably in the vicinity of Tg of the base material to be treated. The treatment time is usually 1 to 72 hours in order to produce sufficient effect of treating. The present invention is not, however, limited to these conditions.

Regarding the present invention, two kinds of polymer aqueous solutions may be used. That is, immersion in the first polymer aqueous solution, treatment, and washing are performed, and thereafter, immersion in the second polymer aqueous solution, and treatment are performed. Accompanying this, the natures of the surface, such as ionicity and nonionicity, can be appropriately changed.

As the polymer having a weight average molecular weight of 200 or more used for the surface treatment of the plastic article, a carboxyl functional polymer, a polymer having the —SO$_3$H group, etc., can be mentioned. As the high molecular weight base, a polymer having the —NH group or the —NH$_2$, group, etc., can be mentioned.

In particular, in the present invention, when the plastic article is hydrogel, a carboxyl functional polymer is preferably used. The carboxyl functional polymer means a polymer having the —COOH group in the molecule. Most of all, a polymer selected from the group consisting of polymethacrylic acid, polyitaconic acid, and copolymers of methacrylic acid, maleic acid, itaconic acid, or maleic anhydride and a reactive vinyl monomer, or a mixture thereof can be appropriately used.

The weight average molecular weight of these carboxyl functional polymers are preferably 5,000 or more, and more preferably are 20,000 or more since the wettability of the surface can be improved without degradation of mechanical properties of the hydrogel. By using the aforementioned high molecular weight carboxyl functional polymers, strong polymer complexes can be formed with the hydrophilic polymers in the hydrogel base materials, and the effects thereof can be maintained for further long term.

As the carboxyl functional polymer, poly acrylic acid and alternative copolymer of maleic anhydride with vinyl monomer can be appropriately used from the viewpoint of the ability of forming polymer complexes, the long term maintenance of the effects, and the available ease of the high molecular weight products.

Regarding the treatment of the hydrogel plastic article with two kinds of polymer aqueous solutions, in the case in which the aqueous solution of the carboxyl functional polymer is used as the first polymer aqueous solution, the non-ionic water-soluble polymer is preferably used as the second polymer aqueous solution. The non-ionic water-soluble polymer means a water-soluble polymer not containing an ionic group, and polyacrylamide, polydimethylacrylamide, polyvinyl pyrrolidone, polyethylene glycol, polyethylene oxide, and polyvinyl alcohol, or a mixture thereof are preferably used. These non-ionic polymers form thin layers of polymer complexes with the carboxyl functional polymers on the thin layers of polymer complexes formed by the immersion treatment in the first aqueous solutions, so that the properties of the surfaces can be changed.

As the preferred embodiments of the surface-treated plastic article according to the present invention, lenses, fibers, films, etc., can be mentioned. In particular, the surface-treated plastic article is appropriately used for optical articles, for example, contact lenses, intraocular lenses, and plastic lenses, from the viewpoint of excellent optical properties, high oxygen permeability, excellent wettability, and mechanical properties, and is also appropriately used for medical devices, such as catheters and artificial kidneys, because of the wettability of the surface and the sliding ease accompanying the wettability.

In the case in which the optical articles according to the present invention are used for optical articles contacting with corneas, such as contact lenses, the optical articles are preferably hydrogel, and the water contents are preferably 15% or more. By this, the movement of the lenses, which is required of the optical articles contacting with corneas, becomes smooth, so that the lenses can be worn with further safety.

EXAMPLES

The present invention will be explained using the following examples, although the present invention is not limited to these examples. Herein, measurements and evaluations were performed in accordance with the following methods.

1. Water Content

The plastic article was subjected to a hydration treatment, and thereafter, the water content (%) was determined based on the following formula:

Water content (%)=(W-WO)/W×100 wherein W designates the weight (g) of the plastic article after the hydration treatment, and WO indicates the weight (g) of the plastic article in a dry state.

2. Dynamic Contact Angle

By using a plastic article having a size of about 5 mm by 10 mm by 0.1 mm, advancing dynamic contact angles relative to the boric acid buffer solution having a pH of 7.1 to 7.3 were measured. The immersion velocity was 0.1 mm/sec, and the depth of the immersion was 7 mm.

3. Static Contact Angle of Water

After water is removed from the surface by blowing with nitrogen gas, the static contact angles of water were measured with a CA-D type contact angle meter, manufactured by Kyowa Kaimen Kagaku K. K., using water treated with the reverse osmosis membrane.

4. Wettability

The plastic article was immersed in the boric acid buffer solution having a pH of 7.1 to 7.3. Thereafter, the plastic article was pulled up, and the appearance of the surface was visually observed so as to evaluate in accordance the following criteria:

⊚: the surface of the plastic article is uniformly wetted;

○: a half or more of the surface area of the plastic article is uniformly wetted;

Δ: a half or more of the surface area of the plastic article is not uniformly wetted; and ×: the surface of the plastic article is hardly wetted.

5. Mechanical Properties

The plastic article having a size of about 15 mm by 10 mm by 0.1 mm was used as a sample, and the modulus and the elongation at break were measured using Tensilon RTM-100 manufactured by Toyo Baldwin K. K. The tensile speed was 100 mm/min, and the chuck interval was 5 mm.

6. Oxygen Permeability

The plastic article having a diameter of 15 mm was used as a sample, and the oxygen permeability coefficient was measured using Seikaken-type film-oxygen permeameter manufactured by Rikaseiki Kogyo K. K. in water at 35° C. The thickness of the sample was adjusted by stacking a plurality of sheets if necessary.

Example 1

60 parts by weight of tris(trimethylsiloxy)silylpropyl methacrylate (abbreviated as TRIS), 40 parts by weight of N,N-dimethylacrylamide (abbreviated as DMAA), 1 part by weight of triethylene glycol dimethacrylate (abbreviated as 3G), and 10 parts by weight of diethylene glycol dimethyl ether (abbreviated as Diglyme) were uniformly mixed. After 0.2 parts by weight of "Darocur1173", manufactured by Ciba Specialty Chemicals, as a polymerization initiator was added thereto, the resulting monomer mixture was degassed in an argon atmosphere. The degassed monomer mixture was injected between plastic molds and was sealed in a glove box in an atmosphere of nitrogen. Then, the light irradiation was performed using an insect collection lamp at an illumination of 1 mW/cm$^2$ for 30 minutes so as to perform polymerization. Subsequently, the molds including the resulting plastic were immersed in diethylene glycol dimethyl ether at 40° C. for 30 minutes, and in addition to this, were immersed at 60° C. for 60 minutes, and then, the resulting plastic article to be treated was released from the molds. As the immersion solution, isopropyl alcohol was substituted for diethylene glycol dimethyl ether, and the remaining monomers were extracted by heating at 60° C. for 16 hours. The resulting plastic article to be treated was washed two times with isopropyl alcohol. Thereafter, the washed plastic article was immersed in a solution composed of 50 parts by weight of isopropyl alcohol and 50 parts by weight of purified water for 30 minutes, and then, was immersed in a solution composed of 25 parts by weight of isopropyl alcohol and 75 parts by weight of purified water for 30 minutes, and furthermore, was immersed in purified water and was left standing for 16 hours, so that isopropyl alcohol was completely removed from the plastic article to produce the plastic article to be treated. The resulting plastic article to be treated was immersed in an aqueous solution, having a pH of 2.3, containing 15% by weight of polyacrylic acid having an average molecular weight of 25,000 at 40° C. for 8 hours. Subsequently, the resulting plastic article was sufficiently washed with purified water, was put in a vial containing a boric acid buffer solution having a pH of 7.1 to 7.3, and was sealed. The resulting vial was put in an autoclave, and was subjected to a boiling treatment at 120° C. for 30 minutes. After the vial was left standing for cooling, the plastic article was taken out of the vial, and was immersed in the boric acid buffer solution having a pH of 7.1 to 7.3. A water content, a dynamic contact angle, wettability, a modulus, an elongation at break, and an oxygen permeability coefficient of the resulting plastic article were measured. The results thereof are shown in Table 1.

Example 2

A surface-treated plastic article was produced in a manner similar to that in Example 1, except that the aqueous solution containing polyacrylic acid in Example 1 was changed to an aqueous solution, having a pH of 2.0, containing 20% by weight of polyacrylic acid having an average molecular weight of 5,000. A water content, a dynamic contact angle, wettability, a modulus, and an elongation at break of the resulting plastic article are shown in Table 1.

Example 3

A surface-treated plastic article was produced in a manner similar to that in Example 1, except that the aqueous solution containing polyacrylic acid in Example 1 was changed to an aqueous solution, having a pH of 3.1, containing 1.2% by weight of polyacrylic acid having an average molecular weight of 250,000. A water content, a dynamic contact angle, wettability, a modulus, and an elongation at break of the resulting plastic article are shown in Table 1.

Comparative Example 1

A plastic article was produced in a manner similar to that in Example 1, except that the treatment with the aqueous solution containing polyacrylic acid in Example 1 was omitted. A water content, a dynamic contact angle, wettability, a modulus, an elongation at break, and an oxygen permeability coefficient of the resulting plastic article are shown in Table 1.

Example 4

A surface-treated plastic article was produced in a manner similar to that in Example 1, except that tris(trimethylsiloxy) silylpropyl methacrylate in Example 1 was changed to 68.75% by weight of the following compound M1 (abbreviated as SiOEMMA), 20.83% by weight of N,N-dimethylacrylamide (abbreviated as DMAA), and 10.42% by weight of N,N-methoxyethylacrylamide (abbreviated as MEAA), and the treatment condition with the aqueous solution containing polyacrylic acid in Example 1 was changed to at 60° C. for 24 hours. A water content, a dynamic contact angle, wettability, a modulus, and an elongation at break of the resulting plastic article are shown in Table 1.

(M1)

Example 5

A surface-treated plastic article was produced in a manner similar to that in Example 4, except that the aqueous solution containing polyacrylic acid in Example 4 was changed to an aqueous solution, having a pH of 11.78, containing 30% by weight of polyethyleneimine having an average molecular weight of 600, and the treatment condition in Example 4 was changed to at 23° C. for 72 hours. A water content, a dynamic contact angle, and wettability of the resulting plastic article are shown in Table 1.

Comparative Example 2

A plastic article was produced in a manner similar to that in Example 5, except that the treatment with the aqueous solution containing polyethyleneimine in Example 5 was omitted. A water content, a dynamic contact angle, wettability, a modulus, and an elongation at break of the resulting plastic article are shown in Table 1.

Example 6

A surface-treated plastic article was produced in a manner similar to that in Example 1, except that tris(trimethylsiloxy)silylpropyl methacrylate in Example 1 was changed to 70% by weight of the following compound M2 (abbreviated as SiMAA2), and 30% by weight of N,N-dimethylacrylamide (abbreviated as DMAA). A water content, a dynamic contact angle, wettability, a modulus, and an elongation at break of the resulting plastic article are shown in Table 1.

(M2)

Example 7

A surface-treated plastic article was produced in a manner similar to that in Example 1, except that tris(trimethylsiloxy)silylpropyl methacrylate in Example 1 was changed to 70% by weight of the following compound M3 (abbreviated as SiMAA3), and 30% by weight of N,N-dimethylacrylamide. A water content, a dynamic contact angle, wettability, a modulus, and an elongation at break of the resulting plastic article are shown in Table 1.

(M3)

Example 8

A surface-treated plastic article was produced in a manner similar to that in Example 1, except that the monomers in Example 1 were changed to 21.33 parts by weight of tris(trimethylsiloxy)silylpropyl methacrylate, 42.67 parts by weight of the compound M1 (abbreviated as SiOMMA), and 36 parts by weight of N,N-dimethylacrylamide (abbreviated as DMAA), and the aqueous solution in Example 1 was changed to an aqueous solution, having a pH of 2.6, containing 5% by weight of polyacrylic acid having an average molecular weight of 150,000. A water content, a dynamic contact angle, wettability, a modulus, an elongation at break, and an oxygen permeability coefficient of the resulting plastic article are shown in Table 1.

Figure 1:
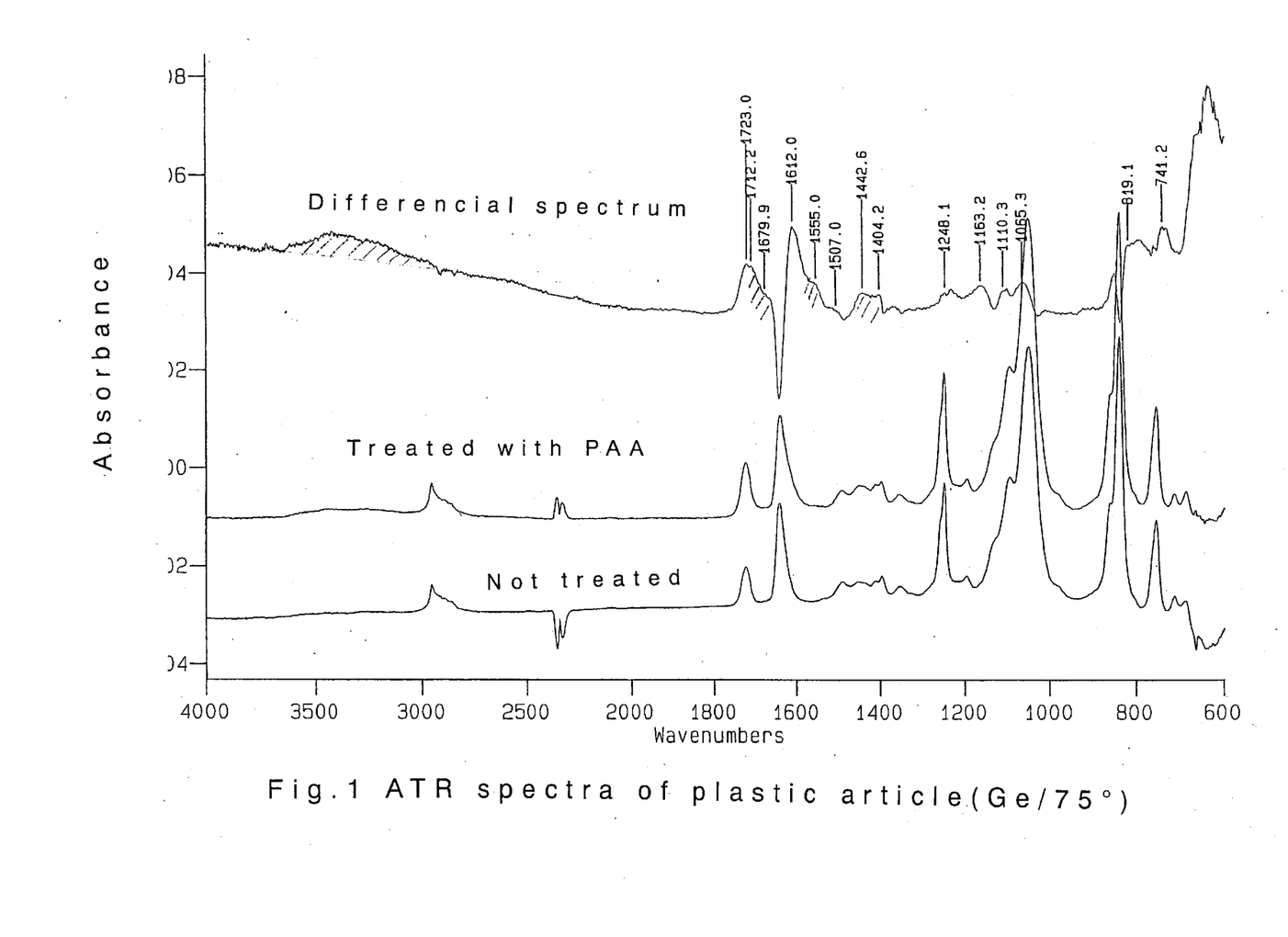
FIG. 1 is a diagram showing ATR spectra of plastic articles treated with PAA and not treated, and a differential spectrum therebetween.

A Fourier transform infrared spectrum of the surface-treated plastic article according to the present invention measured by Attenuated Total Reflection Spectroscopy (FTIR-ATR method) is shown in FIG. 1. The result of the measurement by the FTIR-ATR method regarding the plastic article according to Comparative Example 3, and the differential spectrum, which is obtained by subtracting the measurement result regarding Comparative Example 3 from the measurement result regarding Example 8, are also shown in FIG. 1. As is clear from FIG. 1, regarding the plastic article treated with polyacrylic acid, designated by NS07 (PAA), carboxylic acid (hydroxyl group) is increased as shown by an increase in 3,000 to 3,500 $cm^{-1}$ band and an increase in 1,720 $cm^{-1}$ band, carboxylate is increased as shown by an increase in 1,404 to 1,442 $cm^{-1}$ band and in 1,556 $cm^{-1}$ band, and amide is decreased as shown by a decrease in 1,645 $cm^{-1}$ band compared to the plastic article not treated with polyacrylic acid, designated by NS07 (not treated). The increases of carboxylic acid and carboxylate indicate that polyacrylic acid presents on the surface of the surface-treated plastic article due to some interactions. On the other hand, amide is believed to be derived from dimethylacrylamide which is a hydrophilic component. Since this amide bond is very stable, the amide bond is not normally hydrolyzed by the aqueous solution having a pH of 2.6 or so. Therefore, it is believed that polydimethylacrylamide in the base material for the plastic article and polyacrylic acid formed a polymer complex, a thin layer of the resulting complex was formed on the surface, and as a consequence, the apparent density of the amide bond of dimethylacrylamide was decreased so as to exhibit the aforementioned differential spectrum.

Comparative Example 3

A plastic article was produced in a manner similar to that in Example 8, except that the treatment with the aqueous solution containing polyacrylic acid in Example 8 was omitted. A water content, a dynamic contact angle, wettability, a modulus, an elongation at break, and an oxygen permeability coefficient of the resulting plastic article are shown in Table 1.

Example 9

A surface-treated plastic article was produced in a manner similar to that in Example 8, except that the monomers in Example 8 were changed to 31.5 parts by weight of tris(trimethylsiloxy)silylpropyl methacrylate (abbreviated as TRIS), 31.5 parts by weight of the compound M2 (abbreviated as SiMAA2), and 37 parts by weight of N,N-dimethylacrylamide (abbreviated as DMAA). A water content, a dynamic contact angle, wettability, a modulus, an elongation at break, and an oxygen permeability coefficient of the resulting plastic article are shown in Table 2.

Comparative Example 4

A plastic article was produced in a manner similar to that in Example 9, except that the treatment with the aqueous solution containing polyacrylic acid in Example 9 was omitted. A water content, a dynamic contact angle, wettability, a modulus, an elongation at break, and an oxygen permeability coefficient of the resulting plastic article are shown in Table 2.

Example 10

A surface-treated plastic article was produced in a manner similar to that in Example 1, except that the monomers in Example 1 were changed to 30 parts by weight of tris(trimethylsiloxy)silylpropyl methacrylate (abbreviated as TRIS), 30 parts by weight of tris(trimethylsiloxy)silylpropyl acrylate (abbreviated as TRIS-A), and 40 parts by weight of N,N-dimethylacrylamide (abbreviated as DMAA). A water content, a dynamic contact angle, wettability, a modulus, and an elongation at break of the resulting plastic article are shown in Table 2.

Example 11

30.5 parts by weight of the compound M2 (abbreviated as SiMAA2), 30.5 parts by weight of tris(trimethylsiloxy)silylpropyl methacrylate (abbreviated as TRIS), 39 parts by weight of N,N-dimethylacrylamide (abbreviated as DMAA), 1 part by weight of triethylene glycol dimethacrylate (abbreviated as 3G), and 10 parts by weight of diethylene glycol dimethyl ether (abbreviated as Diglyme) were uniformly mixed. After 0.2 parts by weight of "Darocur1173" manufactured by Ciba Specialty Chemicals, as a polymerization initiator, was added thereto, a plastic article to be treated was produced in a manner similar to that in Example 1. On the other hand, 0.5 g of isobutylene-maleic anhydride copolymer having a molecular weight of 160,000 to 170,000 ("Isoban" 10, manufactured by KURARAY CO., LTD.) was dispersed in 50 ml of 0.65N NaOH solution, and the resulting solution was agitated at 90° C. until the solution become transparent. Thereafter, 3 ml of 1N HCl was added, so that the pH was adjusted to 2.82.

In this polymer aqueous solution, the aforementioned plastic article to be treated was immersed at 40° C. for 5 hours. Subsequently, the resulting plastic article was sufficiently washed with purified water, was put in a vial containing a boric acid buffer solution having a pH of 7.1 to 7.3, and was sealed. The resulting vial was put in an autoclave, and was subjected to a boiling treatment at 120° C. for 30 minutes. After the vial was left standing for cooling, the plastic article was taken out of the vial, and was immersed in the boric acid buffer solution having a pH of 7.1 to 7.3. A water content, a dynamic contact angle, wettability, and an oxygen permeability coefficient of the resulting plastic article were measured. The results thereof are shown in Table 2.

Example 12

Methyl vinyl ether-maleic anhydride copolymer having a molecular weight of 216,000 ("Gantrez" AN-119, manufactured by International Specialty Products Inc.) was dispersed in purified water, and the resulting solution was agitated at 85 to 90° C. so as to produce transparent 10% by weight aqueous solution.

A water content, a dynamic contact angle, wettability, and an oxygen permeability coefficient of the plastic article, produced in a manner similar to that in Example 11, except that the aforementioned methyl vinyl ether-maleic anhydride copolymer was used instead of the isobutylene-maleic anhydride copolymer in Example 11, were measured. The results thereof are shown in Table 2.

Comparative Example 5

A plastic article was produced in a manner similar to that in Example 11, except that the treatment with the aqueous solution containing isobutylene-maleic anhydride copolymer in Example 11 was omitted. A water content, a dynamic contact angle, wettability, and an oxygen permeability coefficient of the resulting plastic article are shown in Table 2.

Example 13

A surface-treated plastic article was produced in a manner similar to that in Example 9, except that the monomers in Example 9 were changed to 30 parts by weight of tris(trimethylsiloxy)silylpropyl methacrylate (abbreviated as TRIS), 30 parts by weight of the compound M2 (abbreviated as SiMAA2), and 40 parts by weight of 2-hydroxyethyl methacrylate (abbreviated as HEMA). A water content, a dynamic contact angle, wettability, a modulus, and an elongation at break of the resulting plastic article are shown in Table 2.

Comparative Example 6

A plastic article was produced in a manner similar to that in Example 13, except that the treatment with the aqueous solution containing polyacrylic acid in Example 13 was omitted. A water content, a dynamic contact angle, and wettability of the resulting plastic article are shown in Table 2.

Example 14

100 parts by weight of 2-hydroxyethyl methacrylate (abbreviated as HEMA), 1 part by weight of triethylene glycol dimethacrylate (abbreviated as 3G), and 0.2 parts by weight of "Darocur1173" manufactured by Ciba Specialty Chemicals were uniformly mixed, and were photopolymerized using an insect collection lamp in a manner similar to that in Example 1. The resulting polymer was released from the molds in purified water, and thereafter, was subjected to a boiling treatment at 120° C. for 30 minutes in purified water using an autoclave so as to produce hydrogel. This hydrogel was immersed in an aqueous solution containing 5% by weight of polyacrylic acid, having a molecular weight of 150,000, at 40° C. for 8 hours. Subsequently, the resulting hydrogel was sufficiently washed with purified water, was put in a vial containing a boric acid buffer solution having a pH of 7.1 to 7.3, and was sealed. The resulting vial was put in an autoclave, and was subjected to a boiling treatment at 120° C. for 30 minutes. After the vial was left standing for cooling, the plastic article was taken out of the vial, and was immersed in the boric acid buffer solution having a pH of 7.1 to 7.3. A water content, a dynamic contact angle, and wettability of the resulting plastic article were measured. The results thereof are shown in Table 2.

Comparative Example 7

A plastic article was produced in a manner similar to that in Example 14, except that the treatment with the aqueous solution containing polyacrylic acid in Example 14 was omitted. A water content, a dynamic contact angle, and wettability of the resulting plastic article are shown in Table 2.

Example 15

52 parts of 2-hydroxyethyl methacrylate, 53.4 parts of 2,6-diisocyanatocaproic acid-β-isocyanatoethyl ester, and 0.01 parts of di-n-butyltin dilaurate were put into a four neck flask provided with an agitator, a thermometer, a reflux condenser, and a nitrogen gas inlet, and were agitated at 50° C. in a nitrogen atmosphere until the absorption assigned to the hydroxyl group disappeared from an infrared absorption spectrum. Next, 300 parts of the following compound M4 having an average molecular weight of 3,000 was added into the aforementioned four neck flask, and the resulting mixture was agitated at 50° C. in a nitrogen atmosphere until the absorption assigned to the isocyanato group disappeared from an infrared absorption spectrum so as to produce siloxane macromer having two double-bonds at each of both ends (abbreviated as tetra-functional macromer).

(M4)

A surface-treated plastic article was produced in a manner similar to that in Example 8, except that the monomers in Example 8 were changed to 30 parts by weight of the aforementioned tetra-functional macromer, 38 parts by weight of tris(trimethylsiloxy)silylpropyl methacrylate (abbreviated as TRIS), and 32 parts by weight of N,N-dimethylacrylamide (abbreviated as DMAA). A water content, a dynamic contact angle, wettability, a modulus, an elongation at break, and an oxygen permeability coefficient of the resulting plastic article were measured. The results thereof are shown in Table 3.

Comparative Example 8

A plastic article was produced in a manner similar to that in Example 15, except that the treatment with the aqueous solution containing polyacrylic acid in Example 15 was omitted. A water content, a dynamic contact angle, wettability, a modulus, an elongation at break, and an oxygen permeability coefficient of the resulting plastic article were measured. The results thereof are shown in Table 3.

Example 16

33 parts by weight of the compound M2 (abbreviated as SiMAA2), 33 parts by weight of the following macromer having double-bond at one end (abbreviated as single-functional macromer) M5 with a molecular weight of about 1,000, (M5)

34 parts by weight of N,N-dimethylacrylamide (abbreviated as DMA), 5 parts by weight of the following macromer (abbreviated as double-functional macromer) M6 having a molecular weight of about 1,900, (M6)

and 10 parts by weight of ethylene glycol diacetate (abbreviated as EGDA) were uniformly mixed. After 0.2 parts by weight of "Darocur1173" manufactured by Ciba Specialty Chemicals, as a polymerization initiator, was added thereto, a plastic article to be treated was produced in a manner similar to that in Example 1.

On the other hand, methyl vinyl ether-maleic anhydride copolymer having a molecular weight of about 2,000,000 ("Gantrez" AN-169, manufactured by International Specialty Products Inc.) was dispersed in purified water, and the resulting solution was agitated at 85 to 90° C. so as to produce transparent 5% by weight aqueous solution.

In this polymer aqueous solution, the aforementioned plastic article to be treated was immersed at 40° C. for 3 hours. Subsequently, the resulting plastic article was sufficiently washed with purified water, was put in a vial containing a boric acid buffer solution having a pH of 7.1 to 7.3, and was sealed. The resulting vial was put in an autoclave, and was subjected to a boiling treatment at 120° C. for 30 minutes. After the vial was left standing for cooling, the plastic article was taken out of the vial, and was immersed in the boric acid buffer solution having a pH of 7.1 to 7.3. A water content, a dynamic contact angle, wettability, a modulus, and an elongation at break were measured. The results thereof are shown in Table 3.

Comparative Example 9

A plastic article was produced in a manner similar to that in Example 16, except that the treatment with the aqueous solution containing methyl vinyl ether-maleic anhydride copolymer in Example 16 was omitted. A water content, a dynamic contact angle, wettability, a modulus, and an elongation at break of the resulting plastic article were measured. The results thereof are shown in Table 3.

Example 17

The plastic article, treated with polyacrylic acid, produced according to Example 9 was immersed in an aqueous solution containing 0.05% of polyacrylicamide, having a molecular weight of about 1,000,000, at 40° C. for 8 hours. Subsequently, the resulting plastic article was sufficiently washed with purified water, was put in a vial containing a boric acid buffer solution having a pH of 7.1 to 7.3, and was sealed. The resulting vial was put in an autoclave, and was subjected to a boiling treatment at 120° C. for 30 minutes. After the vial was left standing for cooling, the plastic article was taken out of the vial, and was immersed in the boric acid buffer solution having a pH of 7.1 to 7.3. The resulting plastic article had a water content of 32.8%, a dynamic contact angle of 34°, a modulus of 105 psi, and an elongation at break of 750%. These values indicated that the nature of the surface was changed compared to that in the case in which only the treatment with polyacrylic acid was performed so as to exhibit the water content of 31%, the dynamic contact angle of 280, the modulus of 91 psi, and the elongation at break of 561%.

In order to confirm this point, an adsorption experiment of lysozyme from egg white was performed. 0.5 g of lysozyme from egg white was dissolved into 100 ml of boric acid buffer solution so as to prepare an artificial foul solution. A sheet of sample was immersed in 1 ml of the resulting foul solution, and was left standing at 35° C. for 20 hours. After completion of the immersion treatment, the sample was taken out and was left standing in the boric acid buffer solution for 5 hours. Thereafter the resulting sample was pulled up and was lightly wiped to remove water. An amount of the adsorbed lysozyme was determined by measuring absorbance at 562 nm using a Micro BCA Protein Assay Reagent Kit manufactured by Pierce Chemical Co., based on a bicinconic acid protein assay method. As a consequence, the adsorption amount in the article treated with polyacrylic acid only was 33 $\mu$g/cm$^2$, although the adsorption amount in the article further treated with the immersion in the polyacrylamide aqueous solution was significantly changed to 150 $\mu$g/cm$^2$.

Example 18

99 parts by weight of methyl methacrylate (abbreviated as MMA), and 1 part by weight of triethylene glycol dimethacrylate (3G) were uniformly mixed. After 0.1 part by weight of 2,2'-azobis-(2,4-dimethylvaleronitrile) (abbreviated as ADVN) as a polymerization initiator was added thereto, the resulting monomer mixture was degassed in an argon atmosphere. The degassed monomer mixture was injected between glass plates and sealed. The polymerization was performed at 40° C. for 10 hours. Subsequently, the temperature was raised from 40° C. to 90° C. over a period of time 24 hours, and was kept at 100° C. for 4 hours so as to produce the plastic article to be treated. The resulting plastic article to be treated was immersed in an aqueous solution, having a pH of 2.6, containing 5% by weight of polyacrylic acid having an average molecular weight of 150,000 at 60° C. for 24 hours. Thereafter, the resulting plastic article was sufficiently washed with purified water. A water content, a static contact angle of water, and wettability of the resulting plastic article were measured. The results thereof are shown in Table 4.

Comparative Example 10

A plastic article was produced in a manner similar to that in Example 18, except that the treatment with the aqueous solution containing polyacrylic acid in Example 18 was omitted. A water content, a static contact angle of water, and wettability of the resulting plastic article were measured. The results thereof are shown in Table 4.

Example 19

39 parts by weight of tetra-functional macromer produced according to Example 15, 49.4 parts by weight of trifluoroethyl methacrylate (abbreviated as 3FM), 4.1 parts by weight of methyl methacrylate (abbreviated as MMA), 4.5 parts by weight of trimethylolpropane trimethacrylate (abbreviated as TMPT), 3 parts by weight of metbacrylic acid (abbreviated as MAA), 0.02 parts by weight of azobisisobutyronitrile (abbreviated as AIBN), and 0.08 parts by weight of azobiscyclohexanecarbonitrile (abbreviated as ACHCN) were mixed and dissolved so as to produce a monomer mixture. The resulting mixture solution was put in a test tube, the monomer mixture was degassed in an argon atmosphere, and thereafter, the test tube was plugged airtight. First, in a constant temperature water bath, heating was performed at 40° C. for 40 hours, at 50° C. for 24 hours, at 60° C. for 16 hours, at 70° C. for 4 hours, and at 90°C. for 2 hours, and furthermore, in a hot-air circulation type oven, the heating was performed at 130° C. for 30 hours so as to produce a rod-like plastic article. The resulting plastic article was cut into the shape of a circle with a diamond cutter, and the surface thereof was polished so as to produce a plastic article to be treated. The plastic article to be treated was immersed in an aqueous solution, having a pH of 2.6, containing 5% by weight of polyacrylic acid having an average molecular weight of 25,000 at 60° C. for 8 hours. Subsequently, the resulting plastic article was sufficiently washed with purified water, was immersed in a boric acid buffer solution having a pH of 7.1 to 7.3 in a vial, and the vial was sealed. The resulting vial was put in an autoclave, and was subjected to a boiling treatment at 120° C. for 30 minutes. After the vial was left standing for cooling, the plastic article was taken out of the vial, and was immersed in the boric acid buffer solution having a pH of 7.1 to 7.3. A water content, a static contact angle of water, and wettability of the resulting plastic article were measured. The results thereof are shown in Table 4.

Comparative Example 11

A plastic article was produced in a manner similar to that in Example 19, except that the treatment with the aqueous solution containing polyacrylic acid in Example 19 was omitted. A water content, a static contact angle of water, and wettability of the resulting plastic article were measured. The results thereof are shown in Table 4.

According to the present invention, a surface-treated plastic article can be provided, in which the surface thereof has superior hydrophilicity not varying with time while maintaining various properties as the plastic article.

In particular, in the case in which the surface-treated plastic articles are optical articles, for example, contact lenses, intraocular lenses, and plastic lenses, the aforementioned superior properties are exhibited, so that superior products can be produced.

TABLE 1

| | | Example 1 | Example 2 | Example 3 | Comp. Example 1 | Example 4 | Example 5 | Comp. Example 2 | Example 6 | Example 7 | Example 8 | Comp. Example 3 |
|---|---|---|---|---|---|---|---|---|---|---|---|---|
| Polymerization composition | TRIS | 60 | | | | | | | | | | 21.33 |
| | SiOEMMA | | | | | | 68.75 | | | | | 42.67 |
| | SiMAA2 | | | | | | | | 70 | | | |
| | SiMMA3 | | | | | | | | | 70 | | |
| | TRIS-A | | | | | | | | | | | |
| | DMAA | | 40 | | | | 20.83 | | | 30 | | 36 |

TABLE 1-continued

|  |  | Example | | | Comp. Example 1 | Example | | Comp. Example 2 | Example | | | Comp. Example 3 |
|---|---|---|---|---|---|---|---|---|---|---|---|---|
|  |  | 1 | 2 | 3 | 1 | 4 | 5 | 2 | 6 | 7 | 8 | 3 |
| Macro-molecule aqueous solution | MEAA |  |  |  |  |  | 10.42 |  |  |  |  |  |
|  | HEMA |  |  |  |  |  |  |  |  |  |  |  |
|  | 3G |  |  |  |  |  | 1 |  |  |  |  |  |
|  | Diglyme |  |  |  |  |  | 10 |  |  |  |  |  |
|  | Darocur 1173 |  |  |  |  |  | 0.2 |  |  |  |  |  |
|  | Macromolecule | Polyacrylic acid | | | — | Polyacrylic acid | Polyethyleneimine | — | Polyacrylic acid | | | — |
|  | Molecular weight | 25,000 | 5,000 | 250,000 | — | 25,000 | 600 | — | 25,000 | 150,000 | | — |
|  | Concentration | 15 wt % | 20 wt % | 1.2 wt % |  | 15 wt % | 30 wt % |  | 15 wt % | 5 wt % |  |  |
|  | pH | 2.3 | 2.0 | 3.1 | — | 2.3 | 11.78 | — | 2.3 | 2.3 | 2.6 | — |
|  | Immersion conditions | 40° C./8 hr | | | — | 60° C./24 r | 23° C./72 hr | — | 40° C./8 hr | | | — |
| Properties of treated article | Water content | 29% | 30% | 26% | 27% | 30% | 27% | 25% | 27% | 18% | 34% | 30% |
|  | Dynamic contact angle | 46° | 37° | 37° | 74° | 43° | 78° | 82° | 71° | 71° | 29° | 91° |
|  | Wettability |  | ◉ |  |  | ◉ | ○ |  |  |  | ◉ |  |
|  | Modulus | 157 psi | 196 psi | 171 psi | 251 psi | 81 psi |  | 73 psi | 114 psi | 256 psi | 74 psi | 132 psi |
|  | Elongation at break | 330% | 530% | 651% | 437% | 100% |  | 292% | 424% | 82% | 473% | 542% |
|  | Oxygen permeability coefficient* | 95 |  |  | 100 |  |  |  |  |  | 87 | 92 |

*unit: $10^{-11}(cm^2/sec)[mlO_2/(ml \cdot hPa)]$

TABLE 2

|  |  | Example 9 | Comp. Example 4 | Example | | | Comp. Example 5 | Example 13 | Comp. Example 6 | Example 14 | Comp. Example 7 |
|---|---|---|---|---|---|---|---|---|---|---|---|
|  |  |  |  | 10 | 11 | 12 |  |  |  |  |  |
| Polymerization composition | TRIS | 31.5 |  | 30 |  | 30.5 |  | 30 |  |  |  |
|  | SiOEMMA |  |  |  |  |  |  |  |  |  |  |
|  | SiMAA2 | 31.5 |  |  |  | 30.5 |  | 30 |  |  |  |
|  | SiMMA3 |  |  |  |  |  |  |  |  |  |  |
|  | TRIS-A |  |  | 30 |  |  |  |  |  |  |  |
|  | DMAA | 37 |  | 40 |  | 39 |  |  |  |  |  |
|  | MEAA |  |  |  |  |  |  |  |  |  |  |
|  | HEMA |  |  |  |  |  |  | 40 |  | 100 |  |
|  | 3G |  |  |  | 1 |  |  |  |  |  |  |
|  | Diglyme |  |  | 10 |  | 1 |  | 10 |  |  |  |
|  | Darocur 1173 |  |  |  | 0.2 |  |  |  |  |  |  |
| Macromolecule aqueous solution | Macromolecule | Polyacrylic acid | — | Polyacrylic acid | Isobutylene Maleic anhydride copolymer | Methyl vinyl ether-Maleic anhydride copolymer | — | Polyacrylic acid | — | Polyacrylic acid | — |
|  | Molecular weight | 150,000 | — | 25,000 | 160,000 to 170,000 | 216,000 | — | 150,000 | — | 150,000 | — |
|  | Concentration | 5 wt % | — | 15 wt % | 1 wt % | 10 wt % | — | 5 wt % | — | 5 wt % | — |
|  | pH | 2.6 | — | 2.3 | 2.82 | 2.04 | — | 2.6 | — | 2.6 | — |
|  | Immersion conditions | 40° C./8 hr | — | 40° C./8 hr | 40° C./5 hr | | — | 40° C./8 hr | — | 40° C./8 hr | — |
| Properties of treated article | Water content | 31% | 29% | 38% | 38.8% | 36.3% | 30.6% | 13% | 11% | 42.9% | 39% |
|  | Dynamic contact angle | 28° | 78° | 52° | 47° | 30° | 72° | 39° | 75° | 29° | 70° |
|  | Wettability | ◉ |  | ◉ | ◉ | ◉ |  | ◉ |  | ◉ |  |
|  | Modulus | 91 psi | 125 psi | 79 psi |  |  |  | 338 psi |  |  |  |
|  | Elongation at break | 561% | 359% | 159% |  |  |  | 61% |  |  |  |
|  | Oxygen permeability coefficient* | 90 | 96 |  | 82 | 85 | 92 |  |  |  |  |

*unit: $10^{-11}(cm^2/sec)[mlO_2/(ml \cdot hPa)]$

TABLE 3

|  | Example 15 | Comp. Example 8 | Example 16 | Comp. Example 9 |
|---|---|---|---|---|
| Polimerization composition | | | | |
| Tetra-functional macromer | 30 | | | |
| TRIS | 38 | | | |
| SiMAA2 | | | 33 | |
| Single-functional macromer | | | 33 | |
| DMAA | 32 | | 34 | |
| 3G | 1 | | | |
| Double-functionalmacromer | | | 5 | |
| Diglyme | 10 | | | |
| EGDA | | | 10 | |
| Darocur 1173 | | 0.2 | | |
| Macromolecule aqueous solution | | | | |
| Macromolecule | Polyacrylic acid | — | Methyl vinyl ether-Maleic anhydride copolymer | — |
| Molecular weight | 150,000 | — | 2,000,000 | — |
| Concentration | 5 wt % | — | 5 wt % | — |
| PH | 2.6 | — | 2.16 | — |
| Immersion conditions | 40° C./8 hr | — | 40° C./3 hr | — |
| Properties of treated article | | | | |
| Water content | 22% | 20% | 33.5% | 30.4% |
| Dynamic contact angle | 31° | 88° | 49° | 76° |
| wettability | ⊙ | | ⊙ | |
| Modulus | 210 psi | 218 psi | 95 psi | 94 psi |
| Elongation at break | 156% | 160% | 200% | 270% |
| Oxygen permeability coefficient* | 118 | 120 | | |

*unit: $10^{-11}(cm^2/sec)[mlO_2/(ml \cdot hPa)]$

TABLE 4

|  | Example 18 | Comp. Example 9 | Example 19 | Comp. Example 11 |
|---|---|---|---|---|
| Polymerization composition | | | | |
| MMA | 99 | | | 4.1 |
| Tetra-functional macromer | | | | 39 |
| 3FM | | | | 49.44 |
| 3G | | | 1 | |
| TMPT | | | | 4.5 |
| ADVN | 0.1 | | | |
| AIBN | | | | 0.02 |
| ACHCN | | | | 0.08 |
| Macromolecule aqueous solution | | | | |
| Macromolecule | Polyacrylic acid | — | Polyacrylic acid | — |
| Molecular weight | 150,000 | — | 25,000 | — |
| Concentration | 5 wt % | — | 5 wt % | — |
| pH | 2.6 | — | 2.6 | — |
| Properties of treated article | | | | |
| Immersion conditions | 60° C./24 hr | — | 60° C./8 hr | — |
| Water content | 0.8% | 0.4% | 1% | 0.5% |
| Static contact angle | 35° | 73° | 83° | 100° |
| Wettability | ○ | | ⊙ | |

What is claimed is:

1. A plastic article comprising a non-crosslinked layer of a carboxyl-functional first polymer on a surface of plastic article substrate, wherein the layer is formed by immersing the surface of said plastic article substrate in an aqueous solution of a carboxyl-functional polymer having a weight average molecular weight of 200 or more to form said layer, wherein the surface of said plastic article is not pretreated prior to said immersing and wherein said aqueous solution contains no coupling agents.

2. A plastic article according to claim 1, wherein the layer further comprises a polymer complex formed from said carboxyl-functional first polymer and a second polymer having a weight average molecular weight of 200 or more and said first polymer.

3. A plastic article according to claim 1 or 2, wherein said plastic article substrate comprises a hydrogel.

4. A plastic article according to claim 3, wherein said hydrogel comprises a silicon atom or a fluorine atom.

5. A plastic article according to claim 4, wherein said hydrogel has a water content greater than 15%.

6. A plastic article according to claim 5, wherein said hydrogel has an oxygen permeability coefficient greater than $50 \times 10^{-11}$ $cm^2/sec/mlO_2/ml$ h.Pa.

7. A plastic article according to claim 5, wherein said first or second polymer is polymethacrylic acid and said plastic article substrate is a contact lens comprising a silicon atom or a fluorine atom.

8. A plastic article according to claim 7, wherein said contact lens has an oxygen permeability coefficient greater than $50 \times 10^{-11}$ $cm^2/sec/mlO_2/ml$ h.Pa.

9. A plastic article according to claim 2, wherein said second polymer is a carboxyl functional polymer.

10. A plastic article according to claim 9, wherein at least one of said first or second carboxyl functional polymers is selected from the group consisting of polyacrylic acid, polymethacrylic acid, polyitaconic acid, a copolymer of a reactive vinyl monomer and methacrylic acid, itaconic acid or maleic acid and mixtures thereof.

11. A plastic article according to claim 1 or 2, wherein said plastic article exhibits infrared absorptions in the 1720 $cm^{-1}$ band, the 1404 $cm^{-1}$ to 1442 $cm^{-1}$ band and the 1556 $cm^{-1}$ band as measured by attenuated total reflection spectroscopy.

12. A plastic article according to claim 2, wherein said second polymer is a nonionic water-soluble polymer.

13. A plastic article according to claim 12, wherein said water-soluble polymer is selected from the group consisting of polyacrylamide, polydimethylacrylamide, polyvinyl pyrrolidone, polyethylene oxide, polyvinyl alcohol and mixtures thereof.

14. An optical device comprising a plastic article substrate suitable for use as an optical device and a non-crosslinked layer of a carboxyl-functional first polymer formed on a surface of said plastic article substrate, wherein the layer is formed by immersing the surface of said plastic article substrate in an aqueous solution of a carboxyl-functional polymer having a weight average molecular weight of 200 or more to form said layer, wherein the surface of said plastic article is not pretreated prior to said immersing and wherein said aqueous solution contains coupling agents.

15. An optical device according to claim 14, wherein the layer further comprises a polymer complex formed from said carboxyl-functional first polymer and a second polymer having a weight average molecular weight of 200 or more.

16. An optical device according to claim 14, wherein said plastic article substrate comprises a hydrogel.

17. An optical device according to claim 16, wherein said hydrogel comprises a silicon atom or a fluorine atom.

18. An optical device according to claim 17, wherein said hydrogel has a water content greater than 15%.

19. An optical device according to claim 18, wherein said hydrogel has an oxygen permeability coefficient greater than $50 \times 10^{-11}$ cm$^2$/sec/mlO$_2$ h.Pa.

20. An optical device according to claim 15, wherein second polymer is a carboxyl functional polymer.

21. An optical device according to claim 20, wherein at least one of said first or second carboxyl functional polymers is selected from the group consisting of polyacrylic acid, polymethacrylic acid, polyitaconic acid and a copolymer of a reactive vinyl monomer and methacrylic acid, itaconic acid or maleic acid, or mixtures thereof.

22. An optical device according to claim 14 or 15, wherein said optical device exhibits infrared absorptions in the 1720 cm$^{-1}$ band, the 1404 cm$^{-1}$ to 1442 cm$^{-1}$ band and the 1556 cm$^{-1}$ band as measured by attenuated total reflection spectroscopy.

23. An optical device according to claim 15, wherein said second polymer is a nonionic water-soluble polymer.

24. An optical device according to claim 23, wherein said water-soluble polymer is selected from the group consisting of polyacrylamide, polydimethylacrylamide, polyvinyl pyrrolidone, polyethylene oxide, polyvinyl alcohol and mixtures thereof.

25. An optical device according to claim 14 or 15, wherein said optical device is a contact lens or an intraocular lens.

* * * * *